United States Patent
Kotha et al.

(10) Patent No.: US 6,982,501 B1
(45) Date of Patent: Jan. 3, 2006

(54) MAGNETIC FLUID POWER GENERATOR DEVICE AND METHOD FOR GENERATING POWER

(75) Inventors: Sanjay Kotha, Falls Church, VA (US); Tirumalai S. Sudarshan, Vienna, VA (US); Ramachandran Radhakrishnan, Falls Church, VA (US)

(73) Assignee: Materials Modification, Inc., Fairfax, VA (US)

( * ) Notice: Subject to any disclaimer, the term of this patent is extended or adjusted under 35 U.S.C. 154(b) by 94 days.

(21) Appl. No.: 10/440,112

(22) Filed: May 19, 2003

(51) Int. Cl.
*H02K 44/00* (2006.01)
(52) U.S. Cl. ............... 310/11; 310/10; 322/2 R
(58) Field of Classification Search ............ 310/10, 310/11, 152; 290/1 R, 54; 204/155; 137/13; 335/51; 322/2 R
See application file for complete search history.

(56) References Cited

U.S. PATENT DOCUMENTS

| | | | |
|---|---|---|---|
| 3,047,507 A | 7/1962 | Winslow | |
| 3,127,528 A * | 3/1964 | Lary et al. ............. | 310/11 |
| 3,287,677 A * | 11/1966 | Mohr .................... | 336/57 |
| 3,488,531 A * | 1/1970 | Rosenweig ............. | 310/10 |
| 3,927,329 A * | 12/1975 | Fawcett et al. ......... | 290/1 R |
| 3,937,839 A | 2/1976 | Strike et al. | |
| 4,064,409 A * | 12/1977 | Redman ................. | 310/306 |
| 4,106,488 A | 8/1978 | Gordon | |
| 4,107,288 A | 8/1978 | Oppenheim et al. | |
| 4,183,156 A | 1/1980 | Rudy | |
| 4,219,945 A | 9/1980 | Rudy | |
| 4,267,234 A | 5/1981 | Rembaum | |
| 4,268,413 A | 5/1981 | Dabisch | |
| 4,303,636 A | 12/1981 | Gordon | |
| 4,321,020 A * | 3/1982 | Mittal .................. | 417/320 |
| 4,323,056 A | 4/1982 | Borrelli et al. | |
| 4,340,626 A | 7/1982 | Rudy | |
| 4,342,157 A | 8/1982 | Gilbert | |
| 4,364,377 A | 12/1982 | Smith | |
| 4,443,430 A | 4/1984 | Mattei et al. | |
| 4,452,773 A | 6/1984 | Molday | |
| 4,454,234 A | 6/1984 | Czerlinski | |
| 4,472,890 A | 9/1984 | Gilbert | |
| 4,501,726 A | 2/1985 | Schröder et al. | |
| 4,545,368 A | 10/1985 | Rand et al. | |
| 4,554,088 A | 11/1985 | Whitehead et al. | |
| 4,574,782 A | 3/1986 | Borrelli et al. | |
| 4,613,304 A * | 9/1986 | Meyer .................. | 431/354 |
| 4,628,037 A | 12/1986 | Chagnon et al. | |
| 4,637,394 A | 1/1987 | Racz et al. | |
| 4,662,359 A | 5/1987 | Gordon | |
| 4,672,040 A | 6/1987 | Josephson | |
| 4,695,392 A | 9/1987 | Whitehead et al. | |
| 4,695,393 A | 9/1987 | Whitehead et al. | |

(Continued)

FOREIGN PATENT DOCUMENTS

DE      3738989    *   5/1989

(Continued)

OTHER PUBLICATIONS

Zahn, M., "Magnetic Fluid and Nanoparticle Applications to Nanotechnology", Journal of Nanoparticle Research 3, pp. 73-78, 2001.*

(Continued)

*Primary Examiner*—Burton Mullins
(74) *Attorney, Agent, or Firm*—Dinesh Agarwal, P.C.

(57) ABSTRACT

A device for generating power includes a fluid including magnetic particles. A source magnetizes the fluid thereby inducing rotations in the magnetic particles for creating a magnetic flux. The rotations of the magnetic particles induce an electromagnetic force in a coil associated with the fluid.

52 Claims, 3 Drawing Sheets

U.S. PATENT DOCUMENTS

| | | | |
|---|---|---|---|
| 4,721,618 A | 1/1988 | Giles et al. | |
| 4,951,675 A | 8/1990 | Groman et al. | |
| 4,992,190 A | 2/1991 | Shtarkman | |
| 4,999,188 A | 3/1991 | Solodovnik et al. | |
| 5,067,952 A | 11/1991 | Gudov et al. | |
| 5,069,216 A | 12/1991 | Groman et al. | |
| 5,079,786 A | 1/1992 | Rojas | |
| 5,108,359 A | 4/1992 | Granov et al. | |
| 5,161,776 A | 11/1992 | Nicholson | |
| 5,178,947 A | 1/1993 | Charmot et al. | |
| 5,180,583 A | 1/1993 | Hedner | |
| 5,202,352 A | 4/1993 | Okada et al. | |
| 5,207,675 A | 5/1993 | Canady | |
| 5,236,410 A | 8/1993 | Granov et al. | |
| 5,348,050 A * | 9/1994 | Ashton | 137/827 |
| 5,354,488 A | 10/1994 | Shtarkman et al. | |
| 5,358,659 A | 10/1994 | Ziolo | |
| 5,374,246 A | 12/1994 | Ray | |
| 5,427,767 A | 6/1995 | Kresse et al. | |
| 5,466,609 A | 11/1995 | Siiman et al. | |
| 5,493,792 A | 2/1996 | Bates et al. | |
| 5,507,744 A | 4/1996 | Tay et al. | |
| 5,525,249 A | 6/1996 | Kordonsky et al. | |
| 5,549,837 A | 8/1996 | Ginder et al. | |
| 5,565,215 A | 10/1996 | Gref et al. | |
| 5,582,425 A | 12/1996 | Skanberg et al. | |
| 5,595,735 A | 1/1997 | Saferstein et al. | |
| 5,597,531 A | 1/1997 | Liberti et al. | |
| 5,599,474 A | 2/1997 | Weiss et al. | |
| 5,624,685 A | 4/1997 | Takahashi et al. | |
| 5,635,162 A | 6/1997 | Fischer | |
| 5,635,215 A | 6/1997 | Boschetti et al. | |
| 5,645,849 A | 7/1997 | Pruss et al. | |
| 5,646,185 A | 7/1997 | Giaccia et al. | |
| 5,650,681 A * | 7/1997 | DeLerno | 310/164 |
| 5,667,715 A | 9/1997 | Foister | |
| 5,670,078 A | 9/1997 | Ziolo | |
| 5,673,721 A * | 10/1997 | Alcocer | 137/13 |
| 5,695,480 A | 12/1997 | Evans et al. | |
| 5,702,630 A | 12/1997 | Sasaki et al. | |
| 5,707,078 A | 1/1998 | Swanberg et al. | |
| 5,714,829 A * | 2/1998 | Guruprasad | 310/306 |
| 5,782,954 A | 7/1998 | Luk | |
| 5,800,372 A | 9/1998 | Bell et al. | |
| 5,813,142 A | 9/1998 | Demon | |
| 5,900,184 A | 5/1999 | Weiss et al. | |
| 5,927,753 A | 7/1999 | Faigle et al. | |
| 5,947,514 A | 9/1999 | Keller et al. | |
| 5,958,794 A | 9/1999 | Bruxvoort et al. | |
| 5,993,358 A | 11/1999 | Gureghian et al. | |
| 6,013,531 A | 1/2000 | Wang et al. | |
| 6,027,664 A | 2/2000 | Weiss et al. | |
| 6,036,226 A | 3/2000 | Brown et al. | |
| 6,036,955 A | 3/2000 | Thorpe et al. | |
| 6,039,347 A | 3/2000 | Maynard | |
| 6,044,866 A | 4/2000 | Rohrbeck | |
| 6,051,607 A | 4/2000 | Greff | |
| 6,076,852 A | 6/2000 | Faigle | |
| 6,083,680 A | 7/2000 | Ito et al. | |
| 6,096,021 A | 8/2000 | Helm et al. | |
| 6,136,428 A | 10/2000 | Truong et al. | |
| 6,149,576 A | 11/2000 | Gray et al. | |
| 6,149,832 A | 11/2000 | Foister | |
| 6,167,313 A | 12/2000 | Gray et al. | |
| 6,186,176 B1 | 2/2001 | Gelbmann | |
| 6,189,538 B1 | 2/2001 | Thorpe | |
| 6,225,705 B1 * | 5/2001 | Nakamats | 290/43 |
| 6,266,897 B1 | 7/2001 | Seydel et al. | |
| 6,274,121 B1 | 8/2001 | Pilgrimm | |
| 6,299,619 B1 | 10/2001 | Greene, Jr. et al. | |
| 6,312,484 B1 | 11/2001 | Chou et al. | |
| 6,315,709 B1 | 11/2001 | Garibaldi et al. | |
| 6,319,599 B1 | 11/2001 | Buckley | |
| 6,335,384 B1 | 1/2002 | Evans et al. | |
| 6,355,275 B1 | 3/2002 | Klein | |
| 6,358,196 B1 * | 3/2002 | Rayman | 600/12 |
| 6,391,343 B1 | 5/2002 | Yen | |
| 6,399,317 B1 | 6/2002 | Weimer | |
| 6,409,851 B1 | 6/2002 | Sethuram et al. | |
| 6,443,993 B1 | 9/2002 | Koniuk | |
| 6,468,730 B2 | 10/2002 | Fujiwara et al. | |
| 6,475,710 B2 | 11/2002 | Kudo et al. | |
| 6,481,357 B1 | 11/2002 | Lindner et al. | |
| 6,489,694 B1 * | 12/2002 | Chass | 310/11 |
| 6,527,972 B1 | 3/2003 | Fuchs et al. | |
| 6,530,944 B2 | 3/2003 | West et al. | |
| 6,548,264 B1 | 4/2003 | Tan et al. | |
| 6,557,272 B2 | 5/2003 | Pavone | |
| 6,663,673 B2 | 12/2003 | Christensen | |
| 6,666,991 B1 | 12/2003 | Atarashi et al. | |
| 6,683,333 B2 | 1/2004 | Kazlas et al. | |
| 6,734,574 B2 * | 5/2004 | Shin | 290/1 R |
| 6,768,230 B2 * | 7/2004 | Cheung et al. | 310/30 |
| 6,789,820 B2 | 9/2004 | Meduvsky et al. | |
| 6,815,063 B1 * | 11/2004 | Mayes | 428/402 |
| 6,871,871 B2 | 3/2005 | Parizat et al. | |
| 2001/0011810 A1 | 8/2001 | Saiguchi et al. | |
| 2001/0016210 A1 | 8/2001 | Mathiowitz et al. | |
| 2001/0033384 A1 | 10/2001 | Luo et al. | |
| 2002/0045045 A1 | 4/2002 | Adams et al. | |
| 2002/0164474 A1 | 11/2002 | Buckley | |
| 2003/0009910 A1 | 1/2003 | Pavone | |
| 2003/0216815 A1 | 11/2003 | Christensen | |
| 2004/0002665 A1 | 1/2004 | Parihar et al. | |
| 2004/0051283 A1 | 3/2004 | Parizat et al. | |
| 2004/0132562 A1 | 7/2004 | Schwenger et al. | |
| 2004/0154190 A1 | 8/2004 | Munster | |

FOREIGN PATENT DOCUMENTS

| | | |
|---|---|---|
| DE | 10240530 | 3/2004 |

OTHER PUBLICATIONS

U.S. Appl. No. 10/157,921—filed May 31, 2002.
PCT Serial No. PCT/US03/14545—filed: May 28, 2003.
U.S. Appl. No. 10/302,962, filed Nov. 25, 2002.
PCT Serial No. PCT/US03/16230—filed: Jun. 25, 2003.
Lubbe, AS et al. "Clinical experiences with magnetic drug targeting: a phase 1 study with 4'-expidoxorubicin in 14 patients with advanced solid tumors", Cancer Research, vol. 56, Issue 20, 4686-4693 (Abstract) (1996).
Sako, M et al., "Embolotherapy of hepatomas using ferromagnetic microspheres, its clinical evaluation and the prospect of its use as a vehicle in chemoembolo-hyperthermic therapy", Gan to kagaku ryoho. Cancer & chemotherapy, vol. 13, No. 4, Pt. 2, 1618-1624 (Abstract) (1986).
Azuma, Y. et al. "Coating of ferric oxide particles with silica by hydrolysis of TEOS", Journal of the Ceramic Society of Japan, 100(5), 646-51 (Abstract) (May 1992).
Atarashi, T. et al. "Synthesis of ethylene-glycol-based magnetic fluid using silica-coated iron particle", Journal of Magnetism and Magnetic Materials, 201, 7-10 (1999).
Homola, A. M. et al., "Novel Magnetic Dispersions Using Silica Stabilized Particles", IEEE Transactions on Magnetics, 22 (5), 716-719 (Sep. 1986).
Giri, A. et al. "AC Magnetic Properties of Compacted FeCo Nanocomposites", Mater. Phys. and Mechanics, 1, 1-10 (2000).

* cited by examiner

MAGNETIC FLUID POWER GENERATOR DEVICE AND METHOD FOR GENERATING POWER

BACKGROUND OF THE INVENTION

The present invention is generally directed to generating power, and more particularly to Nano-Electro-Mechanical System (NEMS) power generators including magnetic fluids.

Micro-Electro-Mechanical Systems (MEMS) are miniaturized devices that integrate mechanical and electrical components on a common silicon substrate. Examples of MEMS mechanical devices are motors, pumps, relays, and actuators. MEMS are used in all types of miniaturized technologies from remote sensors and cellular communications to space based electronic systems and phased-array antennas. All of MEMS mechanical and electrical components require power, therefore unconventional, uninterrupted, and portable power sources for miniaturized technologies are in high demand.

Recently, there has been a strong need for NEMS, nanoscale systems of mechanical elements, such as motors, pumps, relays, and actuators and electronics on a common silicon substrate. The advent of NEMS has increased the need for miniaturized and especially nanoscale power generators.

Magnetic fluids are magnetic field responsive fluids containing magnetic particles coated with a surfactant and dispersed in a carrier liquid. Magnetic field responsive fluids provide variable stress levels created by magnetic coupling of the magnetic particles in the form of chains or bent wall-like structures upon interaction with an external magnetic field. Force absorbing devices, such as dampers, shock absorbers, seals, valves, commonly employ magnetic fluids. However, few devices that generate electric power employ magnetic fluids.

Power generators employing magnetic fluids are magnetically driven generators, while most other types of power generators are electrically driven. Magnetically driven generators have two primary advantages over electrically driven generators. First, they are not subject to any catastrophic failures analogous to electrical breakdown, and second, they have a higher energy density (about two orders of magnitude greater). Thus, it is advantageous to have a power generator for a NEMS utilizing a magnetic fluid to produce electricity.

U.S. Pat. No. 4,064,409 discloses a closed ferrofluid circuit surrounded by a magnet. Heating and cooling the ferrofluid takes advantage of the ferrofluid's magnetic properties to pump the ferrofluid through a solenoid and generate electric power. The device disclosed in this patent is thermally driven, while the present invention is directed to a magnetically driven power generator. In the present invention, alternating and traveling magnetic, fields rather than heating and cooling, take advantage of the magnetic fluid's magnetic properties to pump the magnetic fluid through external pickup coils and generate electric power.

U.S. Pat. No. 4,613,304 discloses a hydrogen gas generator system containing permanently magnetically polarized particles in a hydrogen/oxygen collection chamber. An electrical and/or mechanical pump circulates the magnetic particles in a non-magnetic, non-conductive closed loop of tubing. The circulation of the magnetic particles induces a voltage in a coil surrounding the tubing which may be utilized as an electrical power source. This electrical power source is therefore electrically or mechanically driven, while the present invention is magnetically driven.

U.S. Pat. No. 5,714,829 discloses a method for cooling a system having predictable bursts of heat dissipation using an electromagnetic heat engine. The heat engine includes a magnetic medium having susceptibility that varies with temperature and is magnetized between bursts of heat dissipation to create a magnetic field. An electrical load absorbs energy from the magnetic field by demagnetization. Again, the system disclosed in this patent is thermally driven, while the present invention is directed to a magnetically driven power generator.

U.S. Published Patent Application 2001/0033384 discloses the application of an electric or magnetic field on a thin ferrofluid sample to modulate light. The present invention is designed to generate electricity, not modulate light.

OBJECTS AND SUMMARY OF THE INVENTION

The principal object of the present invention is to provide a magnetically driven power generator device and method for generating power.

An object of the present invention is to provide a magnetically driven power generator device which has high energy density (about two orders of magnitude greater). In addition, the power generator device of the present invention offers increased reliability as it involves no catastrophic failure mechanisms analogous to electrical breakdown.

According to the invention, a pump pumps a magnetic fluid from a reservoir into a non-magnetic, non-conductive loop of tubing. Then an alternating and traveling magnetic field circulates the magnetic fluid through the non-magnetic, non-conductive loop, magnetizes the magnetic fluid, reduces the effective fluid viscosity, and induces rotations in the magnetic particles suspended in the magnetic fluid. The magnetic particle rotations induce a time varying magnetic flux and consequently an electric current through the surrounding external pickup coils. A permanent DC magnet ensures a positive magneto-motive force.

In accordance with the present invention, a device for generating power includes a fluid including magnetic particles. A source magnetizes the fluid thereby inducing rotations in the magnetic particles for creating a magnetic flux. The rotations of the magnetic particles induce an electromagnetic force in a coil associated with the fluid.

BRIEF DESCRIPTION OF THE DRAWINGS

The above and other objects, novel features and advantages of the present invention will become apparent from the following detailed description of the invention, as illustrated in the drawings, in which.

DETAILED DESCRIPTION OF THE INVENTION

Figure 1:
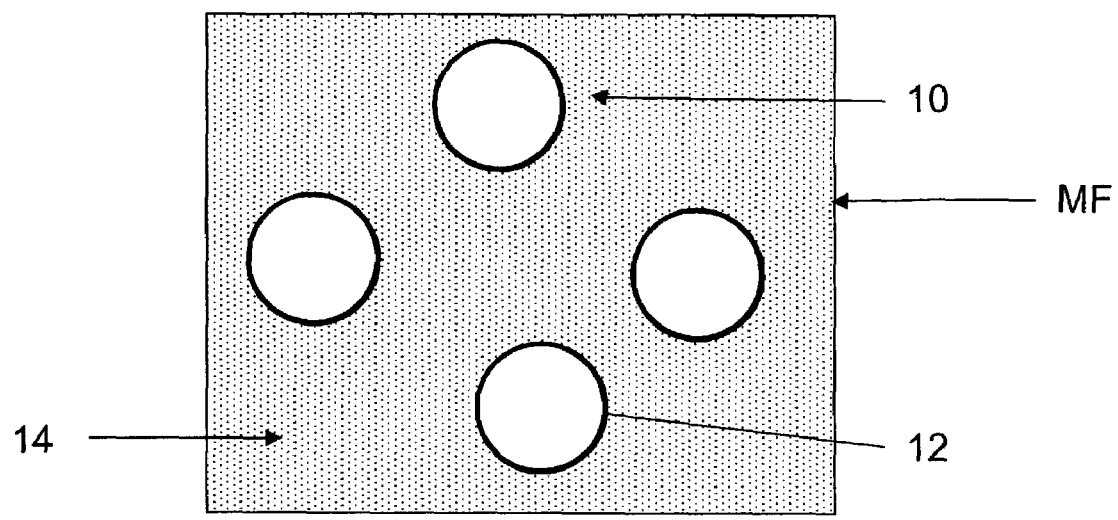
FIG. 1 is a schematic illustration of a magnetic fluid for use in the present invention.

The present invention provides a power generator device PG wherein a magnetic fluid MF produces electricity. The magnetic fluid MF used in the present invention includes a fluid that has magnetic particles 10 coated with a surfactant and/or a coating 12 and dispersed in a carrier liquid 14 (FIG. 1). The surfactant includes long-chain molecules, such as polyethylene glycol, starch, dextran, or a combination thereof, or an electrostatic layer of sodium dodecyl sulfate, sodium salt of cipric acid, hexadecyltrimethyl ammonium bromide, or a combination thereof.

Figure 2:
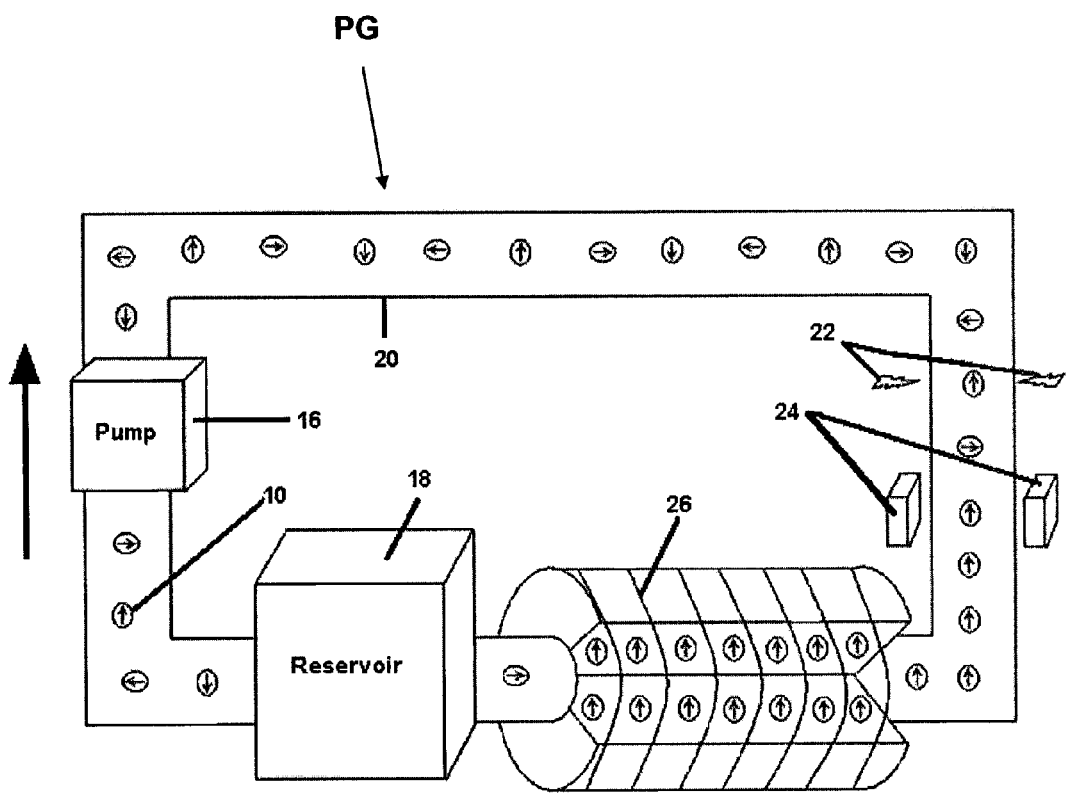
FIG. 2 is a schematic illustration of a power generator device in accordance with the present invention.
Figure 3:
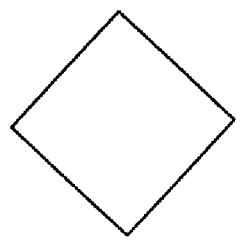
FIG. 3 illustrates various shapes of the magnetic particles for use in the present invention.
Figure 3:
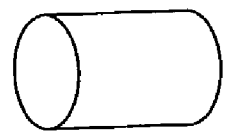
Figure 3:
Figure 3:
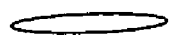
Figure 3:
Figure 3:
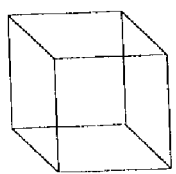
Figure 3:
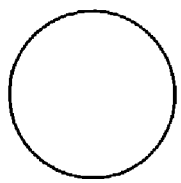

As illustrated in FIG. 2, the power generator device PG of the invention includes a pump 16 that pumps a magnetic fluid out of a reservoir 18 and into a non-magnetic, non-conducting loop of tubing 20. An alternating and traveling magnetic field 22 then circulates the magnetic fluid MF through the non-magnetic, non-conducting loop of tubing 20, part of which is surrounded by a permanent DC magnet 24, causing ferrohydrodynamic rotation. The alternating and traveling magnetic field 22 magnetizes the magnetic fluid MF as the magnetic susceptibility of the magnetic fluid lies between the ferromagnetic and paramagnetic materials. Fluid viscosity acting on the magnetic particles 10 suspended in the magnetic fluid MF causes the magnetization to lag behind the alternating and traveling magnetic field 22 and a torque results. The torque induces rotations in the magnetic particles 10 and decreases the effective fluid viscosity (the decrease in effective fluid viscosity is termed negative viscosity). The effective fluid viscosity is capable of reaching zero or negative values, suggesting that there is close to zero resistance to the motion of the fluid thereby reducing the input energy requirements.

External pickup coils 26 also surround a portion the non-magnetic, non-conductive loop of tubing 20 containing the magnetic fluid MF. Physical motion of the magnetic fluid MF and collective interaction among the magnetic particles 10, causes time variation in the magnetic moments and produces electromagnetic forces in the coils 26. The electromagnetic forces are generated magnetic field source and the particles do not move relative to each other, according to the classical theory of magnetohydrodynamics. The permanent DC magnet 24 assures alignment of the magnetic dipoles so that the magneto-motive forces produced by each magnetic particle add, rather than sum to zero. It is also noted that a non-magnetic solid moving in a magnetized magnetic fluid would disturb the magnetic field and also induce electromagnetic forces in the external pickup coils 26. Therefore, other particles, such as copper, silicon, alumina, aluminum or the like, may be added to the magnetic fluid to increase its power output. Preferably, these particles are non-magnetic and are thermally conducting (such as copper), electrically conducting (such as copper), or non-conducting (such as alumina), or a combination thereof. The device including the magnetic fluid MF, alternating and traveling magnetic fields 22, pump 16, reservoir 18, non-magnetic and non-conductive loop of tubing 20, permanent DC magnet 24, and external pickup coils 26, therefore, acts as an electric power generator.

The magnetic particles may be synthesized by methods commonly known in the art, such as chemical synthesis, sol-gel, chemical co-precipitation, or microwave plasma technique. The microwave plasma technique, described in U.S. Pat. No. 6,409,851 by Sethuram et al. (incorporated herein in its entirety by reference) is the preferred technique as it is unique in that it gives better control over particle size, shape and purity, and can be readily extended to produce different compositions of powders. The magnetic particles may be made of, but are not limited to, iron, iron oxide, cobalt, cobalt oxide, nickel, nickel oxide, an alloy such as steel, or a combination thereof. Preferably, the magnetic particles are made of iron, iron oxide, or a combination thereof. The composition of the particles is important as it determines the magnetic moment of the particles. For example, iron has ten times more saturation magnetization than its oxides, and at least twice as much as its nitrides.

Colloidal particles have an inherent tendency to aggregate and form clusters or agglomerate due to attractive van der Waals (vdW) forces. To stabilize the particles against these attractive forces, it is preferable to introduce a repulsive interparticle force, either by an electrostatic or by a steric means. Electrostatic stabilization utilizes the surface charge typically present on the particles, which is effective in a medium having a high dielectric constant, such as water, while in steric stabilization, a sufficiently thick layer of a polymeric or surfactant molecules is introduced around the particles. The surface layer functions as a steric barrier to prevent particle agglomeration, and thereby ensures stability of the fluid. The surface layer also prevents dissolution of the magnetic materials. This technique is preferred for the present invention. The particles are coated with a surfactant, and/or coating by adsorption of surfactant, and/or coating molecules onto the particles in the presence of ultrasonic irradiation in a high shear field. The types of surfactants that may be utilized in the present invention include, but are not limited to, polyethylene glycol, lecithin, oleic acid, or Surfynol® surfactants (available from Air Products). The types of coatings that may be utilized in the present invention include, but are not limited to, silica, gold, silver, platinum, steel, cobalt, carbon, a polymer, or a combination thereof. The polymer can be polyethylene glycol, polystyrene, dextran, or a combination thereof. Preferably, the particles are only coated with lecithin or Surfynol® surfactants (available from Air Products).

The magnetic particles coated with a surfactant are dispersed in a carrier liquid by high shear mixing followed by ultrasonification to form a homogenous fluid. The carrier liquid helps to retain the fluidity of the magnetic fluid. It is also important as it partially determines the effective fluid viscosity. Carrier liquids are water based and oil based liquids, such as glycerol/water and/or mineral oil mixtures. Preferably, the carrier liquid is water, hydraulic oil, mineral oil, silicone oil, or biodegradable oils such as cocoa oil, or a combination thereof.

The average diameter or size of the magnetic particles can be from about 1 nm to about 1000 nm. The preferred size is about 10 nm to 500 nm, while the most preferred size is about 10 nm to 100 nm. Due to their small size, the magnetic particles remain suspended and are subjected to minimal settling.

The shape of the particles is important for two reasons. First, the magnetic effect is dependent upon the particle volume fraction, which in turn is a function of the particle shape. For instance, needle-shaped particles exhibit similar magnetic effect at concentrations ten times smaller than spherical particles because of larger surface area per volume. Second, the flow characteristics of the particles in a liquid medium are dependent upon their shape. The shapes utilized in this invention include, but are not limited to, spherical, needle-like, cubic, irregular, cylindrical, diamond, oval, or a combination thereof.

The particulate volume or weight fraction is also important as the magnetic character and zero field viscosity are dependent upon the particulate volume or weight fraction. Zero field viscosity refers to the viscosity of the magnetic fluid when it is not acted upon by a magnetic field. A magnetic fluid with a larger particulate volume or weight fraction exhibits greater magnetic character and zero field viscosity than a magnetic fluid with a smaller particulate volume or weight fraction. Preferably, the particulate weight fraction is about 1% to 95%.

EXAMPLE

Ultrafine powders of iron with a particle size less than about 20 nm were produced using the proprietary microwave plasma chemical synthesis process described in U.S. Pat. No. 6,409,851 by Sethuram et al. Vapors of iron pentacarbonyl were fed into the plasmatron with argon as the plasma gas. The plasma gas flow rate was about 0.003–0.0034 m$^3$/min and that of the carrier gas was about 0.0003–0.0004 m$^3$/min. The plasma temperature was about 900–950° C., the powder feed rate was about 50–60 gm/hr, and the quenching water flow rate was about 2.0–2.5 liter/min at 20° C. The reactor column diameter was about 48 mm and its length was about 10". The microwave forward power was about 4 kW, the reflected power was about 0.7 kW, and the operating frequency was about 2450 MHZ.

The iron particles were coated with polyethylene glycol in solution phase and dispersed in water by high-speed shear mixing and ultrasonification.

While this invention has been described as having preferred sequences, ranges, steps, materials, or designs, it is understood that it includes further modifications, variations, uses and/or adaptations thereof following in general the principle of the invention, and including such departures from the present disclosure as those come within the known or customary practice in the art to which the invention pertains, and as may be applied to the central features hereinbeforesefforth, and fall within the scope of the invention and of the limits of the appended claims.

What is claimed is:

1. A device for generating power, comprising:
 a) a fluid comprising magnetic particles;
 b) a source for magnetizing said fluid thereby inducing rotations in the magnetic particles for creating a magnetic flux;
 c) a coil associated with said fluid;
 d) said magnetizing source comprising an alternating and traveling magnetic field;
 e) said magnetic fluid flowing through a generally non-magnetic, non-conducting line;
 f) means for aligning magnetic dipoles of the particles in a generally common direction;
 g) a reservoir for comprising said fluid; and
 h) a pump for pumping said fluid from said reservoir into said line.

2. The device of claim 1, wherein:
 a) said fluid comprises core particles of a magnetic material.

3. The device of claim 2, wherein:
 a) said core particles comprise coated particles.

4. The device of claim 2, wherein:
 a) said core particles have an average diameter of about 1 nm to 1000 nm.

5. The device of claim 2, wherein:
 a) said core particles have an average diameter of about 10 nm to 500 nm.

6. The device of claim 2, wherein:
 a) said core particles have an average diameter of about 10 nm to 100 nm.

7. The device of claim 2, wherein:
 a) said magnetic material is selected from the group consisting of iron, iron oxide, cobalt, cobalt oxide, nickel, nickel oxide, an alloy, and a combination thereof.

8. The device of claim 2, wherein:
 a) said core particles comprise a coating of a surfactant.

9. The device of claim 8, wherein:
 a) said surfactant is selected from the group consisting of polyethylene glycol, lecithin, oleic acid, Surfynol®, and a combination thereof.

10. The device of claim 2, wherein:
 a) said core particles comprise a coating selected from the group consisting of a ceramic material, a metallic material, a polymer material, and a combination thereof.

11. The device of claim 10, wherein:
 a) the coating is selected from the group consisting of silica, gold, silver, platinum, steel, cobalt, carbon, polyethylene glycol, polystyrene, dextran, and a combination thereof.

12. The device of claim 2, wherein:
 a) said core particles comprise first and second successive coatings.

13. The device of claim 12, wherein:
 a) said first coating comprises a coating of a surfactant; and
 b) said second coating comprises a coating of a material selected from the group consisting of a ceramic material, a metallic material, a polymer material, and a combination thereof.

14. The device claim 13, wherein:
 a) said surfactant is selected from the group consisting of polyethylene glycol, lecithin, oleic acid, Surfynol®, and a combination thereof.

15. The device of claim 14, wherein:
 a) said second coating is selected from the group consisting of silica, gold, silver, platinum, steel, cobalt, carbon, polyethylene glycol, polystyrene, dextran, and a combination thereof.

16. The device of claim 4, wherein:
 a) said core particles are coated with a surfactant and dispersed in a carrier fluid.

17. The device of claim 16, wherein:
 a) said carrier fluid comprises a water-based or an oil-based carrier fluid.

18. The device of claim 16, wherein:
 a) said carrier fluid is selected from the group consisting of water, hydraulic oil, mineral oil, silicone oil, biodegradable oil, and a combination thereof.

19. The device of claim 16, wherein:
 a) the fraction of said core particles is about 1–95%.

20. The device of claim 4, wherein:
 a) said core particles comprise a general shape selected from the group consisting of spherical, needle-like, cubic, irregular, cylindrical, diamond, oval, and a combination thereof.

21. The device of claim 2, further comprising:
 a) core particles of a non-magnetic material.

22. The device of claim 21, wherein:
 a) said core particles of a non-magnetic material comprise particles of a thermally conducting material, electrically conducting material, a non-conducting material, or a combination thereof.

23. A device for generating power, comprising:
 a) a fluid for flowing through a generally non-magnetic, non-conducting line;
 b) said fluid comprising magnetic particles;
 c) an alternating and traveling magnetic field for inducing rotations in the magnetic particles for creating a magnetic flux;
 d) a coil associated with said line;
 e) means for aligning magnetic dipoles of the magnetic particles in a generally common direction;

f) a reservoir associated with said line for comprising said fluid; and g) a pump for pumping said fluid from said reservoir into said line.

24. The device of claim 23, wherein:

a) said fluid comprises core particles of a magnetic material.

25. The device of claim 24, wherein:

a) said core particles comprise coated particles.

26. The device of claim 24, wherein:

a) said core particles have an average diameter of about 1 nm to 1000 nm.

27. The device of claim 24, wherein:

a) said core particles have an average diameter of about 10 nm to 500 nm.

28. The device of claim 24, wherein:

a) said core particles have an average diameter of about 10 nm to 100 nm.

29. The device of claim 24, wherein:

a) said magnetic material is selected from the group consisting of iron, iron oxide, cobalt, cobalt oxide, nickel, nickel oxide, an alloy, and a combination thereof.

30. The device of claim 24, wherein:

a) said core particles comprise a coating of a surfactant.

31. The device of claim 30, wherein:

a) said surfactant is selected from the group consisting of polyethylene glycol, lecithin, oleic acid, Surfynol®, and a combination thereof.

32. The device of claim 24, wherein:

a) said core particles comprise a coating selected from the group consisting of a ceramic material, a metallic material, a polymer material, and a combination thereof.

33. The device of claim 32, wherein:

a) the coating is selected from the group consisting of silica, gold, silver, platinum, steel, cobalt, carbon, polyethylene glycol, polystyrene, dextran, and a combination thereof.

34. The device of claim 24, wherein:

a) said core particles comprise first and second successive coatings.

35. The device of claim 34, wherein:

a) said first coating comprises a coating of a surfactant; and b) said second coating comprises a coating of a material selected from the group consisting of a ceramic material, a metallic material, a polymer material, and a combination thereof.

36. The device of claim 35, wherein:

a) said surfactant is selected from the group consisting of polyethylene glycol, lecithin, oleic acid, Surfynol®, and a combination thereof.

37. The device of claim 36, wherein:

a) said second coating is selected from the group consisting of silica, gold, silver, platinum, steel, cobalt, carbon, polyethylene glycol, polystyrene, dextran, and a combination thereof.

38. The device of claim 26, wherein:

a) said core particles are coated with a surfactant and dispersed in a carrier fluid.

39. The device of claim 38, wherein:

a) said carrier fluid comprises a water-based or an oil-based carrier fluid.

40. The device of claim 38, wherein:

a) said carrier fluid is selected from the group consisting of water, hydraulic oil, mineral oil, silicone oil, biodegradable oil, and a combination thereof.

41. The device of claim 38, wherein:

a) the fraction of said core particles is about 1–95% by weight of said carrier fluid.

42. The device of claim 26, wherein:

a) said core particles comprise a general shape selected from the group consisting of spherical, needle-like, cubic, irregular, cylindrical, diamond, oval, and a combination thereof.

43. The device of claim 24, further comprising:

a) core particles of a non-magnetic material.

44. The device of claim 43, wherein:

a) said core particles of a non-magnetic material comprise particles of a thermally conducting material, electrically conducting material, a non-conducting material, or a combination thereof.

45. A method of generating power, comprising the steps of:

a) flowing a fluid comprising magnetic particles in a generally non-magnetic, non-conducing line;

b) magnetizing the fluid by an alternating and traveling magnetic field thereby inducing rotations in the magnetic particles for creating a magnetic flux;

c) aligning magnetic dipoles of the rotating magnetic particles in a generally common direction; and d) inducing an electromagnetic force in a coil associated with the line.

46. A device for generating power, comprising:

a) a fluid comprising magnetic particles;

b) a source for magnetizing said fluid thereby inducing rotations in the magnetic particles for creating a magnetic flux;

c) a coil associated with said fluid;

d) said fluid comprising core particles of a magnetic material; and e) said core particles comprising a coating of a surfactant.

47. The device of claim 46, wherein:

a) said surfactant is selected from the group consisting of polyethylene glycol, lecithin, oleic acid, Surfynol®, and a combination thereof.

48. The device of claim 46, wherein:

a) said core particles comprise a coating selected from the group consisting of a ceramic material, a metallic material, a polymer material, and a combination thereof.

49. The device of claim 48, wherein:

a) the coating is selected from the group consisting of silica, gold, silver, platinum, steel, cobalt, carbon, polyethylene glycol, polystyrene, dextran, and a combination thereof.

50. The device of claim 46, wherein:

a) said core particles comprise first and second successive coatings.

51. The device of claim 50, wherein:

a) said first coating comprises a coating of a surfactant; and b) said second coating comprises a coating of a material selected from the group consisting of a ceramic material, a metallic material, a polymer material, and a combination thereof.

52. A device for generating power, comprising:
a) a fluid for flowing through a generally non-magnetic, non-conducting line;
b) said fluid comprising magnetic particles;
c) an alternating and traveling magnetic field for inducing rotations in the magnetic particles for creating a magnetic flux;
d) a coil associated with said line;
e) means for aligning magnetic dipoles of the magnetic particles in a generally common direction;
f) said fluid comprising core particles of a magnetic material; and
g) said core particles comprising a coating of a surfactant.

* * * * *